(12) United States Patent
Whittaker

(10) Patent No.: US 8,435,292 B2
(45) Date of Patent: May 7, 2013

(54) METHODS FOR LIGAMENT RECONSTRUCTION

(75) Inventor: Gregory R. Whittaker, Stoneham, MA (US)

(73) Assignee: DePuy Mitek, Inc., Raynham, MA (US)

( * ) Notice: Subject to any disclaimer, the term of this patent is extended or adjusted under 35 U.S.C. 154(b) by 1490 days.

(21) Appl. No.: 11/306,238

(22) Filed: Dec. 20, 2005

(65) Prior Publication Data

US 2007/0162122 A1 Jul. 12, 2007

(51) Int. Cl.
*A61F 2/08* (2006.01)

(52) U.S. Cl.
USPC .................. 623/13.14; 623/13.12; 623/13.13; 606/321

(58) Field of Classification Search ................ 623/13.11, 623/13.12, 13.13, 13.14, 13.15, 13.16, 13.17, 623/13.18, 13.19, 13.2; 606/321, 144, 148, 606/228, 86 R, 92–94, 105
See application file for complete search history.

(56) References Cited

U.S. PATENT DOCUMENTS

| | | | |
|---|---|---|---|
| 1,627,894 A * | 5/1927 | Goff ................................. 144/7 |
| 3,805,300 A * | 4/1974 | Tascon-Alonso et al. . 623/13.14 |
| 4,676,798 A | 6/1987 | Noiles |
| 4,879,617 A * | 11/1989 | Sampietro et al. ............ 360/265 |
| 4,898,156 A | 2/1990 | Gatturna et al. |
| 4,899,743 A | 2/1990 | Nicholson et al. |
| 4,968,315 A | 11/1990 | Gatturna |
| 5,013,391 A * | 5/1991 | Hutter et al. .................. 156/578 |
| 5,147,362 A | 9/1992 | Goble |
| 5,356,413 A | 10/1994 | Martins et al. |
| 5,372,599 A | 12/1994 | Martins |
| 5,397,356 A * | 3/1995 | Goble et al. .................. 606/304 |
| 5,431,651 A | 7/1995 | Goble |
| 5,704,747 A * | 1/1998 | Hutter et al. .................... 411/70 |
| 6,325,804 B1 | 12/2001 | Wenstrom, Jr. et al. |
| 6,387,129 B2 | 5/2002 | Rieser et al. |
| 6,610,079 B1 | 8/2003 | Li et al. |
| 6,620,185 B1 | 9/2003 | Harvie et al. |
| 6,652,592 B1 | 11/2003 | Grooms et al. |
| 6,654,077 B1 * | 11/2003 | Bui ................................ 349/58 |
| 6,733,529 B2 | 5/2004 | Whelan |
| 6,752,830 B1 | 6/2004 | Goble et al. |
| 6,808,528 B2 * | 10/2004 | Justin ............................ 606/916 |
| 2001/0041937 A1 | 11/2001 | Rieser et al. |

(Continued)

FOREIGN PATENT DOCUMENTS

CA  2351768    12/2001
EP  1180351 A2  2/2002

(Continued)

OTHER PUBLICATIONS

Office Action, Canadian Patent Application No. 2,571,736, dated Feb. 11, 2009.

(Continued)

*Primary Examiner* — Jan Christopher Merene

(57) ABSTRACT

Methods and devices are provided for fixing a ligament graft in a bone tunnel. In general, the methods and devices involve affixing a ligament graft within a bone tunnel using an adhesive. A fixation device can be inserted through the ligament graft in a direction transverse to an axis of the tunnel to maintain the ligament graft in contact with the adhesive. The fixation device can be removed when the adhesive is cured such that the ligament graft is fixed in the tunnel.

27 Claims, 11 Drawing Sheets

U.S. PATENT DOCUMENTS

| | | | |
|---|---|---|---|
| 2002/0019635 A1* | 2/2002 | Wenstrom et al. | 606/72 |
| 2002/0156476 A1 | 10/2002 | Wilford | |
| 2003/0083662 A1 | 5/2003 | Middleton | |
| 2004/0087953 A1* | 5/2004 | Singhatat et al. | 606/72 |
| 2004/0117014 A1 | 6/2004 | Bryant | |
| 2004/0267263 A1 | 12/2004 | May | |
| 2005/0203623 A1 | 9/2005 | Steiner et al. | |
| 2005/0273003 A1 | 12/2005 | Walters et al. | |

FOREIGN PATENT DOCUMENTS

| | | |
|---|---|---|
| EP | 1 481 651 | 12/2004 |
| JP | 2003-010198 A | 1/2003 |
| WO | 94/28799 | 12/1994 |
| WO | 99/51159 | 10/1999 |

OTHER PUBLICATIONS

Extended European Search Report issued Jan. 16, 2008 for Application No. 06256429.9 (7 pages).

Japanese Office Action issued Sep. 27, 2011 for Application No. 2006-341637 (6 pages).

* cited by examiner

FIG. 10
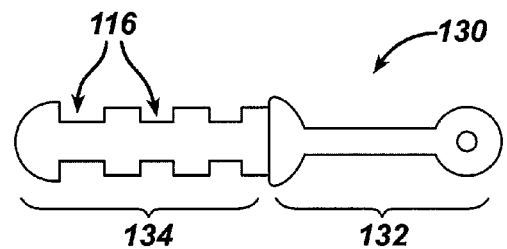
FIG. 11A        FIG. 11B        FIG. 11C
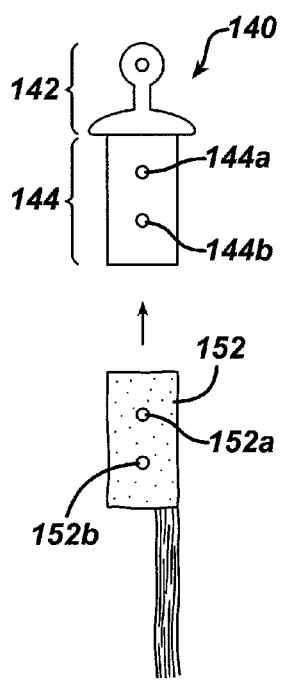 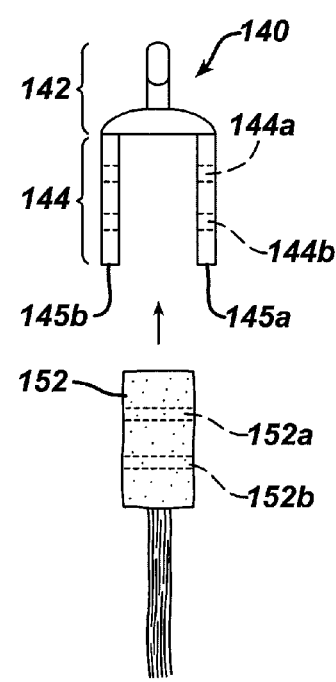 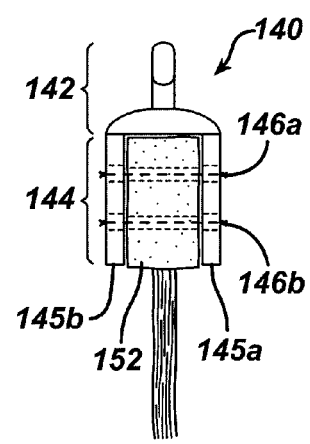

METHODS FOR LIGAMENT RECONSTRUCTION

FIELD OF THE INVENTION

The present invention relates to methods and devices for affixing ligament grafts in bone tunnels.

BACKGROUND OF THE INVENTION

Joint injuries may commonly result in the complete or partial detachment of ligaments, tendons and soft tissues from bone. Tissue detachment may occur in many ways, e.g., as the result of an accident such as a fall, overexertion during a work-related activity, during the course of an athletic event, or in any one of many other situations and/or activities. These types of injuries are generally the result of excess stress or extraordinary forces being placed upon the tissues.

In the case of a partial detachment, commonly referred to under the general term "sprain," the injury frequently heals without medical intervention, the patient rests, and care is taken not to expose the injury to undue strenuous activities during the healing process. If, however, the ligament or tendon is completely detached from its attachment site on an associated bone or bones, or if it is severed as the result of a traumatic injury, surgical intervention may be necessary to restore full function to the injured joint. A number of conventional surgical procedures exist for re-attaching such tendons and ligaments to bone.

One such procedure involves the re-attachment of the detached tissue using "traditional" attachment devices such as staples, sutures, and bone screws. Such traditional attachment devices have also been used to attach tendon or ligament grafts (often formed from autologous tissue harvested from elsewhere in the body) to the desired bone or bones. In one procedure, a damaged anterior cruciate ligament ("ACL") is replaced in a human knee. Initially bone tunnels are formed through the tibia and femur at the points of normal attachment of the anterior cruciate ligament. Next, a ligament graft with a bone graft on one of its ends is sized so as to fit within the bone tunnels. Suture is then attached to the bone graft and thereafter passed through the tibia and femoral bone tunnels. The bone graft is then pulled through the tibial tunnel and up into the femoral tunnel using the suture. As this is done, the ligament graft ligament extends back out of the femoral tunnel, across the interior of the knee joint, and then through the tibial tunnel. The free end of the ligament graft ligament resides outside the tibia, at the anterior side of the tibia. Next, a bone screw is inserted between the bone graft and the wall of femoral bone tunnel so as to securely lock the bone graft in position by a tight interference fit. Finally, the free end of the ligament graft ligament is securely attached to the tibia.

In another ACL reconstruction procedure, aligned femoral and tibial tunnels are initially formed in a human knee. A bone graft with a ligament graft attached thereto is passed through the tunnels to a blind end of the femoral tunnel where the block is fixed in place by an anchor. The ligament extends out of the tibial tunnel, and the end is attached to the tibia cortex by staples or the like. Alternatively, the end of the ligament may be fixed in the tibial tunnel by an anchor or by an interference screw. Various types of ligament and/or suture anchors for attaching soft tissue to bone are also well known in the art. A number of these devices are described in detail in U.S. Pat. Nos. 4,898,156, 4,899,743, 4,968,315, 5,356,413, and 5,372,599, all of which are commonly assigned to Mitek Surgical Products, Inc., a Johnson &Johnson company, and which are incorporated by reference in their entirety.

One known method for anchoring bone grafts in bone tunnels is through a "cross-pinning" technique, in which a pin, screw, or rod is driven into the bone transversely to the bone tunnel so as to intersect the bone graft and thereby cross-pin the bone graft in the bone tunnel. In order to provide for proper cross-pinning of the bone graft in the bone tunnel, a drill guide is generally used. The drill guide serves to ensure that the transverse passage is positioned in the bone so that it will intersect the appropriate tunnel section and the bone graft.

While cross-pinning is effective, there is a continuing need for improved methods and devices for fixing a ligament graft in a bone tunnel.

BRIEF SUMMARY OF THE INVENTION

The present invention generally provides methods and devices for fixing a ligament graft in a bone tunnel. In one exemplary embodiment, the method can include drilling a first tunnel in bone and inserting a ligament graft at least partially into the first tunnel. An adhesive is introduced into the first tunnel, and a fixation device is inserted through the ligament graft in a direction substantially transverse to an axis of the tunnel to maintain the ligament graft in contact with the adhesive. The cross-pin can be removed when the adhesive is cured such that the ligament graft is fixed in the first tunnel.

While the method can be used in a variety of surgical procedures, in one exemplary embodiment the method is used to repair an anterior cruciate ligament. Thus, the ligament graft can be at least partially inserted into a femoral or tibial tunnel formed in a femur or tibia, and the adhesive is introduced into the femoral or tibial tunnel. A fixation device, such as a cross-pin, can be inserted through a transverse tunnel formed in the femur or tibia and intersecting the femoral or tibial tunnel. In certain exemplary embodiments, the transverse tunnel can include a sleeve disposed therein and defining a pathway to the femoral or tibial tunnel. The fixation device is effective to maintain a first end of the ligament graft in the femoral or tibial tunnel in contact with the adhesive. A second end of the ligament graft can then be tensioned and fixed in the other one of the femoral or tibial tunnel, while the adhesive is drying. Once the adhesive is cured, the fixation device can be removed.

The first tunnel can have a variety of configurations, and it can extend only partially through the femur or tibial, or fully through the femur or tibia. In one embodiment, the first tunnel includes an end wall formed therein. The transverse tunnel can intersect the first tunnel adjacent the end wall. The adhesive can thus be introduced through the transverse tunnel such that the adhesive is disposed adjacent to the end wall of the first tunnel. In one exemplary embodiment, the ligament graft is positioned a distance apart from the end wall of the first tunnel prior to introducing the adhesive, and it is pulled toward the end wall and into contact with the adhesive after the adhesive is introduced into the first tunnel. The ligament graft can optionally be pulled through the first tunnel using a suture attached thereto.

In other embodiments, the ligament graft can be directly adhered to the first tunnel, or alternatively it can be coupled to an anchor, such as a bone graft. Where an anchor is used, the fixation device can be inserted through the anchor and the adhesive can be disposed around and optionally within the anchor. In yet another embodiment, the adhesive can be formed from a bioabsorbable material, such that it is eventually absorbed by the body. Alternatively, the adhesive can be a non-absorbable adhesive. In yet another embodiment, the fixation device can be adapted to prevent adhesion between the adhesive and the fixation device. For example, the fixation device can include a protective coating disposed thereon, or it can be formed from a protective material, such as a fluoropolymer plastic resin. The sleeve disposed within the transverse tunnel can also include a protecting coating, or it can be formed from a protective material.

In other embodiments, a method for fixing a ligament graft in a bone tunnel is provided and includes coupling an anchor to the bone graft, introducing the anchor and bone graft into a bone tunnel, and introducing an adhesive into the bone tunnel such that the adhesive surrounds at least a portion of the anchor, thereby affixing the anchor within the bone tunnel. The anchor can have a variety of configurations, but in one embodiment it has a first portion that is adhered to the bone tunnel, and a second portion that mates to the bone graft. The first portion can include a post with an eyelet formed on a terminal end thereof. In order to introduce the anchor and bone graft into a bone tunnel, a suture can be attached to the eyelet and tensioned the suture to pull the bone graft into the bone tunnel. The second portion of the anchor can also have a variety of configurations. For example, it can include threads formed thereon for threading the second portion into the bone graft. In another embodiment, the second portion can be mated to the bone graft using sutures. In particular, the second portion can include opposed arms, and the bone graft can be mated to the opposed arms by passing at least one suture through the opposed arms and through the bone graft.

In yet another embodiment, a ligament graft is provided and includes a bone graft having a ligament extending therefrom, and an anchor having a first portion mated to the bone graft, and a second portion having at least one surface feature adapted to receive an adhesive for adhesively mating the second portion to a bone tunnel. The surface feature on the second portion of the anchor can be, for example, an eyelet having an opening extending therethrough, at least one cut-out portion, or other surface features.

In other aspects, a method for fixing a ligament graft in a bone tunnel is provided and includes modifying the bone graft with a ligament attached thereto to include at least one cut-out portion, introducing the bone graft into a bone tunnel, and introducing an adhesive into the bone tunnel such that the adhesive surrounds at least a portion of the bone graft and extends into the at least one cut-out portion, thereby affixing the bone graft within the bone tunnel. The bone graft can be modified by, for example, forming a plurality of grooves around or on the bone graft, forming at least one thru-bore in the bone graft, etc.

In yet another embodiment, a method for fixing a ligament graft in a bone tunnel is provided and includes coupling a soft tissue ligament to an anchor, introducing the anchor into a bone tunnel, and introducing an adhesive into the bone tunnel such that the adhesive surrounds at least a portion of the anchor, thereby affixing the anchor with the soft tissue ligament extending therefrom within the bone tunnel. The anchor can include a first portion having surface features formed thereon that receive the adhesive therebetween to mate the first portion within the bone tunnel, and a second portion having a mating element that mates to a soft tissue graft. The mating element can be, for example, an eyelet.

BRIEF DESCRIPTION OF THE DRAWINGS

The invention will be more fully understood from the following detailed description taken in conjunction with the accompanying drawings, in which:

FIG. 10 is a side perspective view of another embodiment of an anchor configured to mate to a bone graft and to be affixed within a bone tunnel to anchor the bone graft within the bone tunnel, the anchor having annual grooves for receiving an adhesive;

FIG. 11A is a side view of another embodiment of an anchor and a bone graft, each having suture bores formed therein for mating the bone graft to the anchor;

FIG. 11B is another side view of the anchor and bone graft shown in FIG. 11A;

FIG. 11C is a side view of the anchor and bone graft shown in FIGS. 11A and 11B mated to one another using sutures;

DETAILED DESCRIPTION OF THE INVENTION

The present invention provides methods and devices for fixing a ligament graft in a bone tunnel. The various methods and devices disclosed herein can be used in a variety of surgical procedures, however the methods and devices are particularly useful for repairing an anterior cruciate ligament (ACL) in a human knee. In an ACL repair, the torn ACL is replaced with a ligament graft which is anchored to the tibia and femur. The term "ligament graft," as used herein, is intended to include natural materials, such as autografts, allografts, and xenografts, including harvested ligaments and tendons, as well as synthetic materials. The ligament graft can also include an anchoring element attached thereto for anchoring the graft to the tibia and femur. For example, the ligament graft can include a bone graft, plug, or other member, attached to one or both terminal ends thereof. The term "bone graft," as used herein, in intended to include natural materials, such as autografts, allografts, and xenografts, as well as synthetic materials.

A person skilled in the art will appreciate that the various methods and devices disclosed herein can be used in a variety of surgical procedures, and that the particular configuration of the ligament graft can vary depending on the intended use, and virtually any ligament graft known in the art can be used with the methods disclosed herein.

FIGS. 1-8 illustrate one exemplary method for anchoring a ligament graft in a bone tunnel, and in particular in femoral and tibial tunnels of a human knee. In general, the method includes drilling a tunnel in bone and inserting a ligament graft at least partially into the tunnel. An adhesive is introduced into the tunnel, and a fixation device is inserted through the ligament graft in a direction transverse to an axis of the tunnel to maintain the ligament graft in contact with the adhesive. The fixation device can be removed when the adhesive is cured such that the ligament graft is fixed in the tunnel. The use of a fixation device to maintain the ligament graft in the tunnel while the adhesive cures allows an opposed end of the ligament graft to be tensioned and fixed using the same or a different anchoring technique. The method is described in connection with certain exemplary procedures for preparing bone tunnels and inserting a ligament graft into the bone tunnels. For example, in certain exemplary methods, the ligament graft is affixed in the femoral tunnel prior to affixing it in the tibial tunnel. However, a person skilled in the art will appreciate that the ligament graft can be affixed in the tibial tunnel first or at the same time. A person skilled in the art will also appreciate that a variety of other procedures known in the art can be used to prepare the bone tunnels and to the insert a ligament graft into the bone tunnels.

Figure 1:
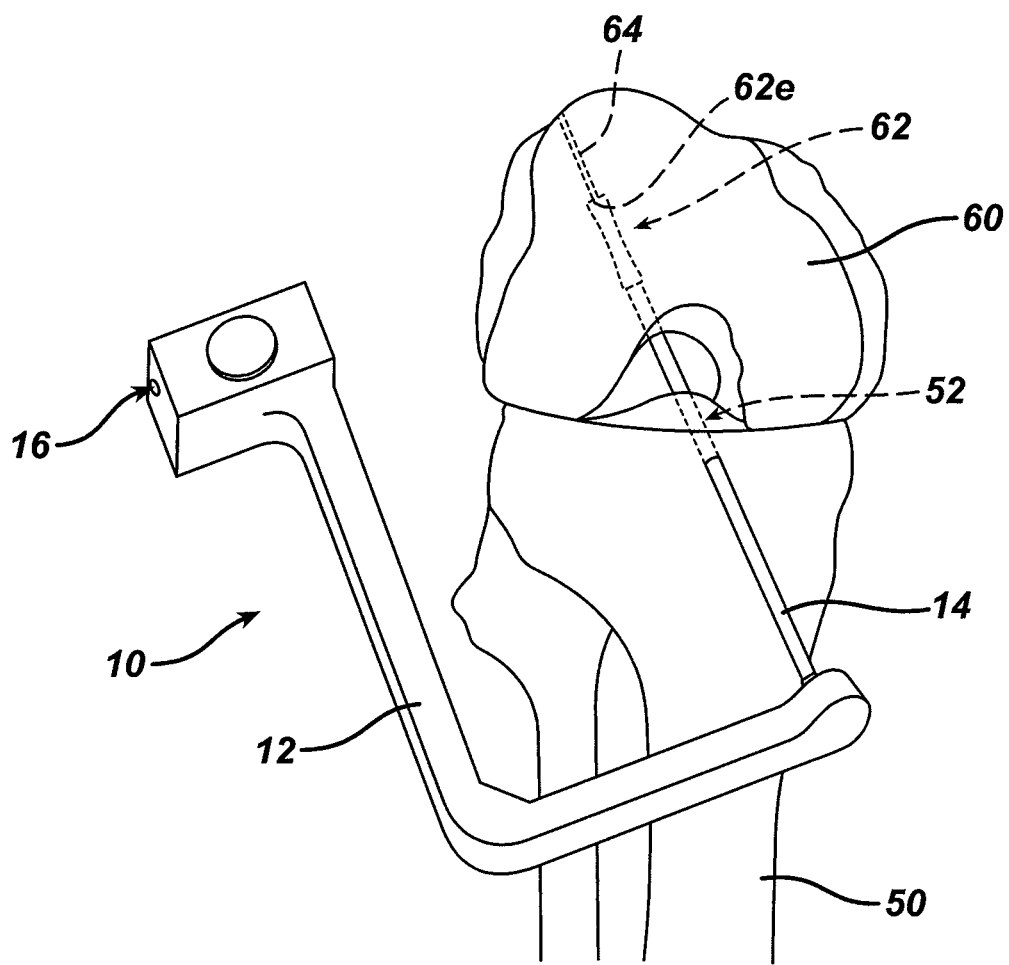
FIG. 1 illustrates a human knee and a guide device having a cannulated guide rod extending through bone tunnels formed in the tibia and femur.

Referring first to FIG. 1, a bone tunnel is drilled through the tibia 50 and femur 60, using conventional surgical equipment and techniques, to form a tibial tunnel 52 and femoral tunnel 62. The tibial and femoral tunnels 52, 62 can extend completely through the tibia and femur 50, 60, however in an exemplary embodiment the femoral tunnel 62 terminates part way through the femur 60 such that a femoral socket is formed. A suture tunnel 64 can optionally extend through the remainder of the femur 60 in longitudinal alignment with the femoral tunnel 62 to allow a suture to pass therethrough and pull and graft into the tunnels 52, 62, as will be discussed in more detail below. The suture tunnel 64 preferably has an inner diameter that is less than an inner diameter of the femoral tunnel, such that a terminal end of the femoral tunnel defines an end wall 62e.

Figure 2:
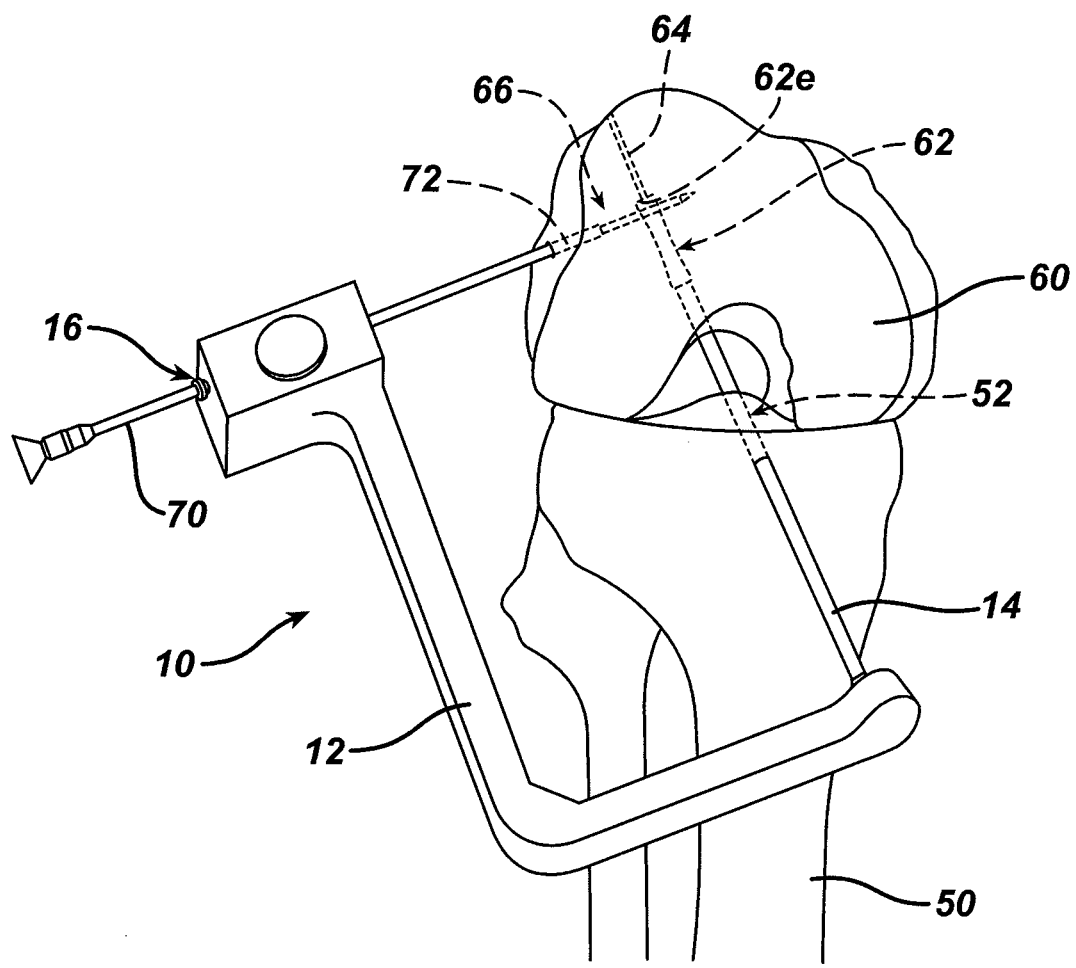
FIG. 2 illustrates the human knee and guide device of FIG. 1, showing a sleeve and trocar assembly being inserted through the femur to form a transverse tunnel that intersects the femoral tunnel.
Figure 3:
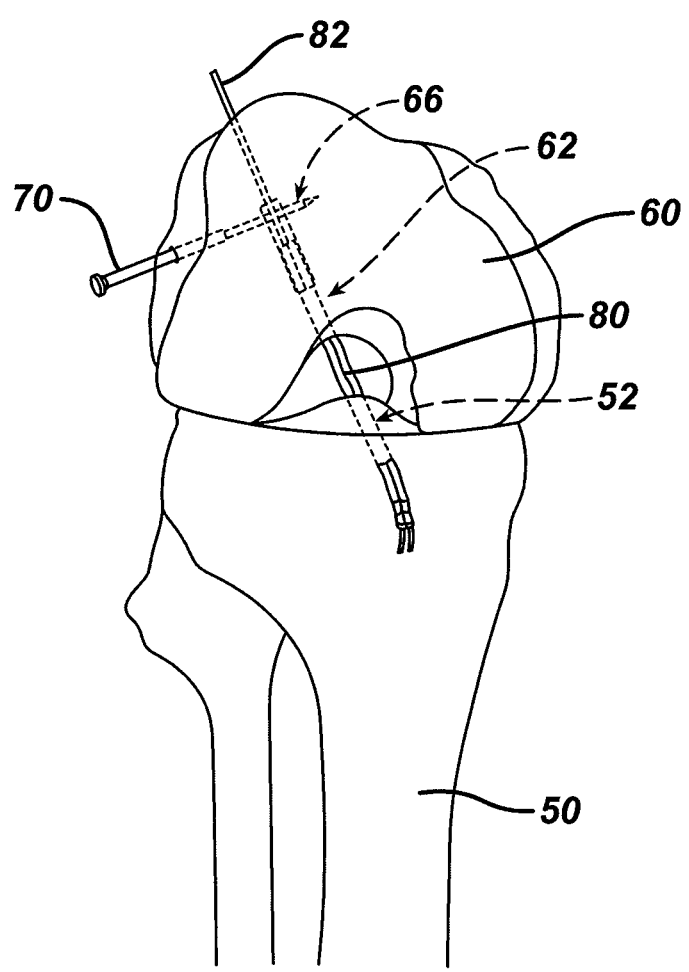
FIG. 3 illustrates the human knee of FIG. 2 with the guide device and the trocar removed, leaving the sleeve extending into the transverse tunnel, and a ligament graft extending through the tibial tunnel and into the femoral tunnel.

Once the tibial and femoral tunnels 52, 62 are prepared, a transverse tunnel can be formed in the femur. The transverse tunnel preferably intersects the femoral tunnel 62 such that a pathway is formed through the transverse tunnel to the femoral tunnel 62. This pathway can be used to inject an adhesive into the femoral tunnel 62, as will be discussed in more detail below. As shown in FIG. 1, a guide device 10 can optionally be used to locate and align the transverse tunnel. As shown, the guide device 10 generally includes an L-shaped frame 12 having a cannulated guide rod 14 extending from one end thereof, and a housing with an opening 16 formed therethrough on an opposed end thereof. The cannulated guide rod 14 can be inserted through the tibial tunnel 52 and the femoral tunnel 62 to maintain the guide frame 12 in a fixed position. As shown in FIG. 2, a sleeve and trocar assembly 70, 72 can then be inserted through the opening 16 in the housing on the guide frame 12, and drilled into the lateral side of the femur until the sleeve and trocar abut the cannulated guide rod 14. The transverse tunnel 66 will thus extend through the femur and into the femoral tunnel 62, preferably at a location substantially adjacent to the distal end wall 62e of the femoral tunnel. A person skilled in the art will appreciate that the transverse tunnel 66 can extend at any angle relative to the femoral tunnel 62. After the transverse tunnel 66 is completely formed, the trocar 72 can be removed leaving the sleeve 70 in place, as shown in FIG. 3. The sleeve 70 can be inserted partially into the transverse tunnel 66, such that it does not extend into the femoral tunnel 62, or alternatively the sleeve 70 can at least partially extend into the femoral tunnel 62. This will allow the sleeve 70 to function as a stop for the ligament graft, as will be discussed in more detail below. The procedure can, however, be performed without the use of the sleeve 70.

After the tibial, femoral, and transverse tunnels 52, 62, 66 are formed, a ligament graft 80 can be introduced into the tibial and femoral tunnels 52, 62. While various procedures known in the art can be used to introduce the ligament graft 80 into the tibial and femoral tunnels 52, 62, in one exemplary embodiment a suture 82 can be attached to a leading end of the ligament graft 80 and it can be threaded through the tibial and femoral tunnels 52, 62 using, for example, a guide pin or other device. Tension can then be applied to the suture to pull the ligament graft 80 up through the tibial tunnel 52 and at least partially into the femoral tunnel 62. As shown in FIG. 3, the ligament graft 80 can be pulled to a location that is spaced a distance apart from the end wall 62e of the femoral tunnel, such that the ligament graft 80 stops short of the transverse tunnel 66. Where the sleeve 70 extends into the femoral tunnel 62, the sleeve 70 will prevent the ligament graft 80 from being fully advanced into contact with the end surface 62e of the femoral tunnel 62.

Figure 4:
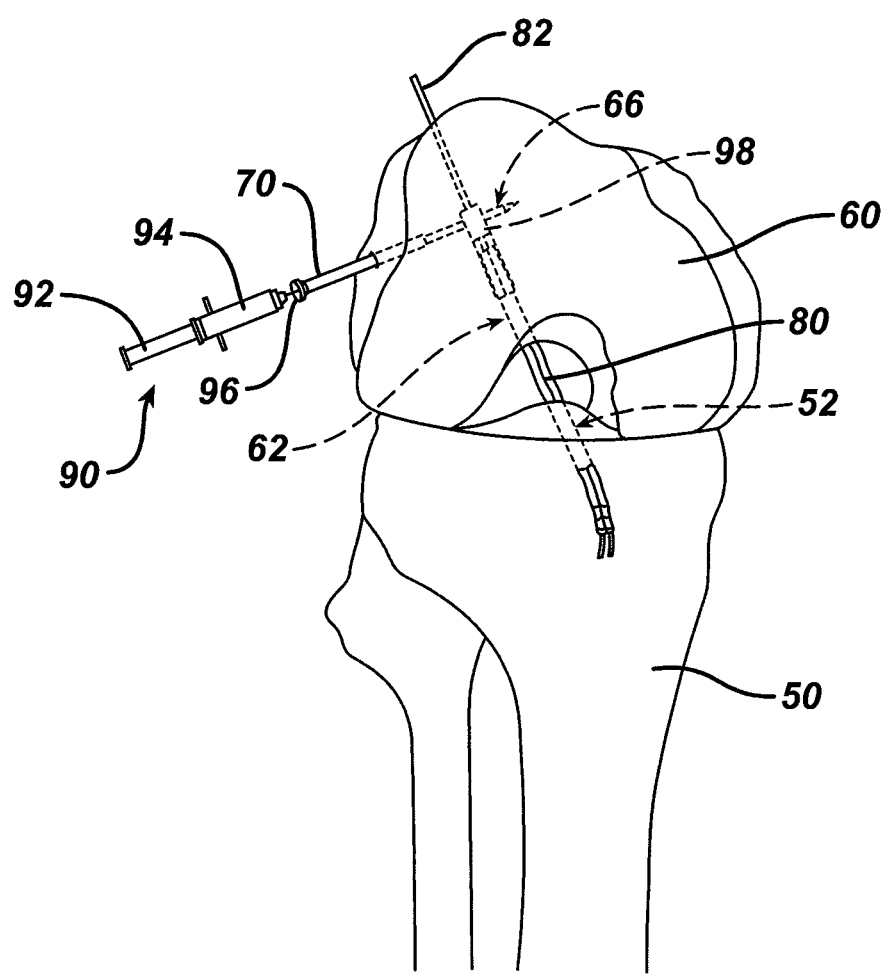
FIG. 4 illustrates the human knee of FIG. 3, showing a syringe inserted through the sleeve in the transverse tunnel and injecting an adhesive into the femoral tunnel.

As shown in FIG. 4, once the ligament graft 80 is positioned within the femoral tunnel 62 the surgeon can inject an adhesive 98 into the femoral tunnel 62 to secure the ligament graft 80 therein. While the adhesive 98 can be injected through any of the tunnels using a variety of techniques, in the illustrated exemplary embodiment the adhesive 98 is injected through the transverse tunnel 66 using a syringe 90. In particular, the syringe 90 is placed through the sleeve 70 in the transverse tunnel 66 and into the femoral tunnel 62, and a plunger 92 on the syringe 90 is then moved into a barrel 94 to eject the adhesive 98 from the barrel 94, through the needle 96, and into the femoral tunnel 62. The amount of adhesive 98 can vary, but in an exemplary embodiment, the adhesive 98 fills a terminal end portion of the femoral tunnel 62 adjacent to the end surface 62e.

Figure 5:
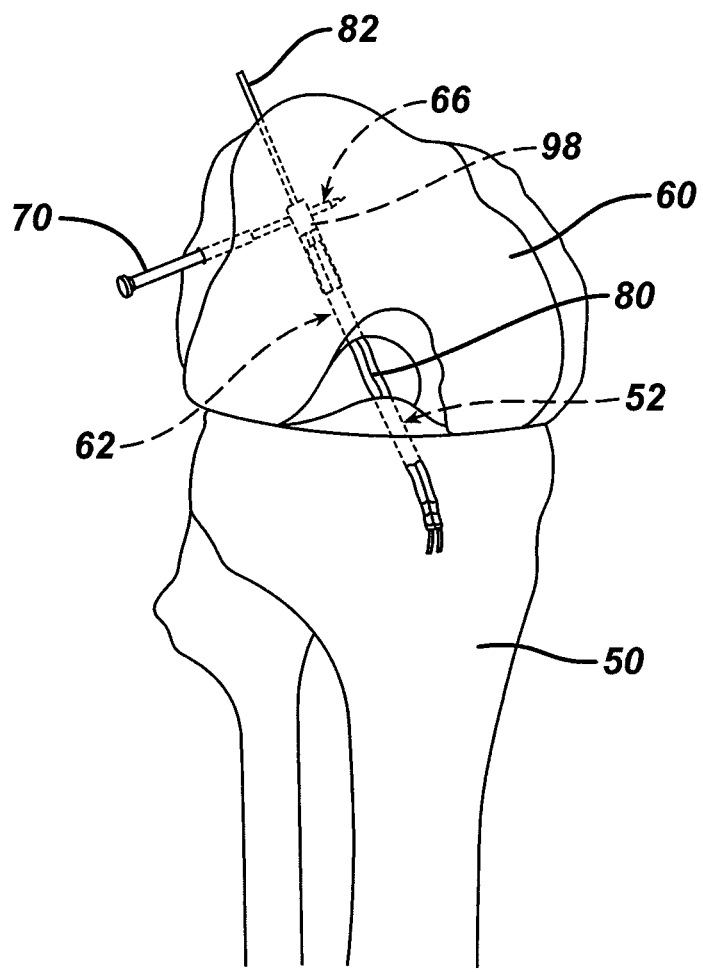
FIG. 5 illustrates the human knee of FIG. 4, showing the ligament graft pulled further into the femoral tunnel and into contact with the adhesive such that the adhesive surrounds an end of the ligament graft.

Once the terminal end portion of the femoral tunnel 62 is filled with the adhesive 98, the suture 82 is further tensioned to pull the ligament graft 80 into the terminal end portion such that the ligament graft 80 abuts the end wall 62e of the femoral tunnel 62, as shown in FIG. 5. As a result, the ligament graft 80 is brought into contact with the adhesive 98, which is spread in and around the ligament graft 80. The adhesive 98 thus extends between the end surface 62e and the ligament graft 80, and forms a cap that surrounds the ligament graft 80, and optionally that extends into portions of the ligament graft 80. In other embodiments, the ligament graft 80 can be fully pulled into the femoral tunnel 62 and into contact with the end surface 62e, and then the adhesive 98 can be injected into the tunnel 62 until it completely surrounds and encapsulates an end portion of the ligament graft 80.

Figure 6:
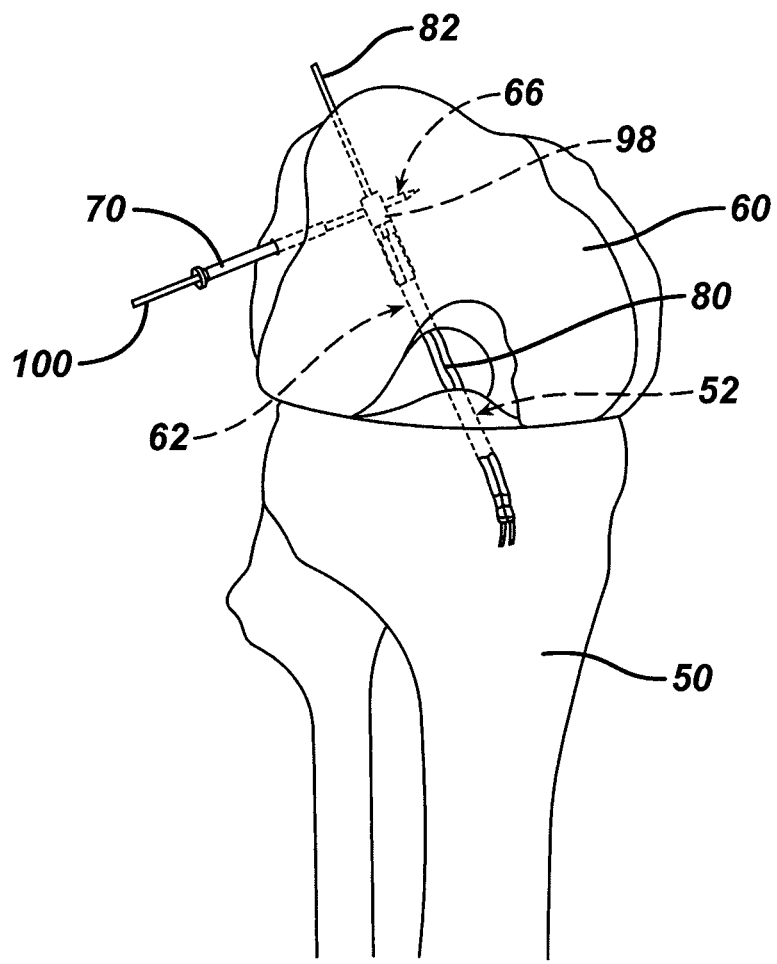
FIG. 6 illustrates the human knee of FIG. 5, showing a cross-pin being inserted through the sleeve, into the transverse tunnel, and through the ligament graft to maintain the ligament graft in a fixed position within the femoral tunnel.
Figure 7:
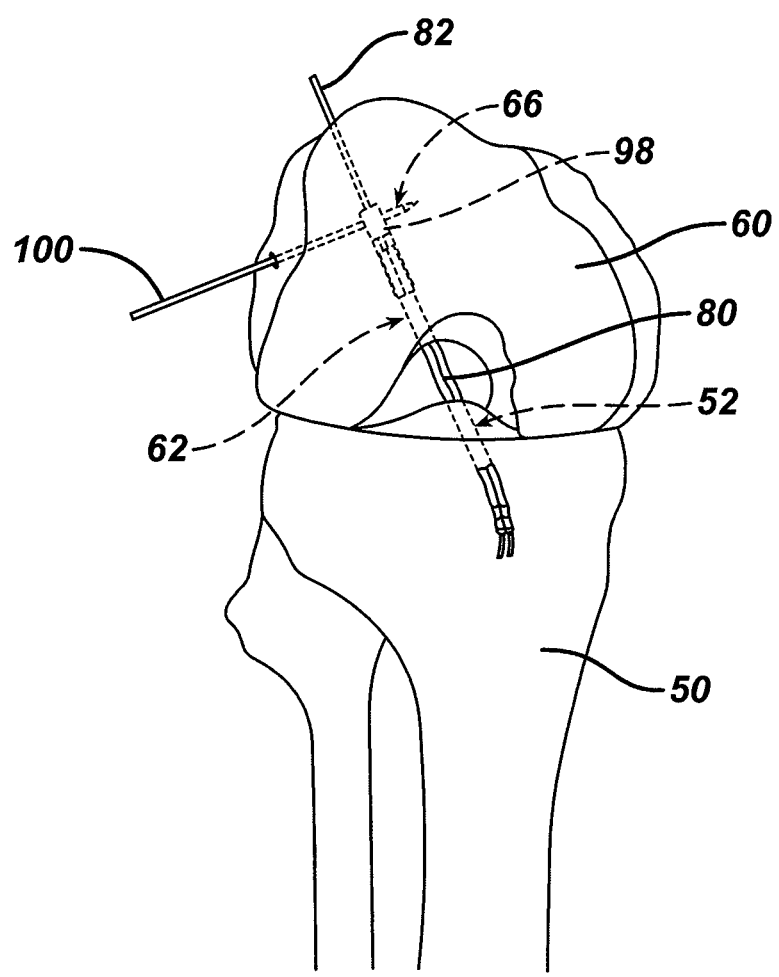
FIG. 7 illustrates the human knee of FIG. 6 showing the sleeve removed leaving the cross-pin in place.
Figure 8:
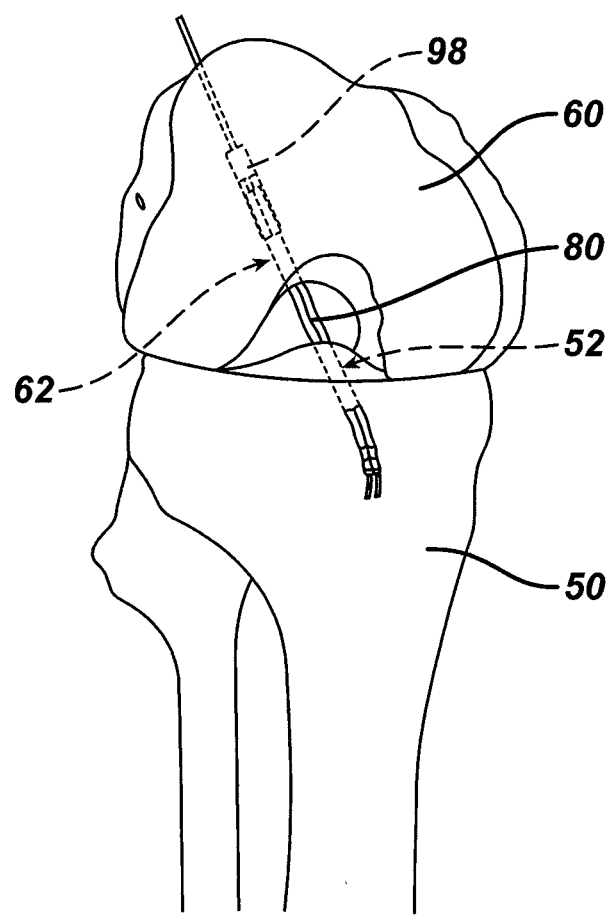
FIG. 8 illustrates the human knee of FIG. 7 showing the cross-pin removed after the adhesive has cured.

Since the adhesive 98 can take time to cure, the first end of the ligament graft 80 can be temporarily secured in the femoral tunnel 62 using a fixation device. FIG. 6 illustrates one exemplary embodiment of a fixation device in the form of a cross-pin 100 that is used to secure the ligament graft 80 in the femoral tunnel 62. As shown, the cross-pin 100 is in the form of an elongate member that is inserted through the sleeve 70 in the transverse tunnel and through a loop formed in the terminal end of the ligament graft 80. The cross-pin 100 can also extend across the femoral tunnel 62 and into a further portion of the transverse tunnel. In an exemplary embodiment, the cross-pin 100 has a length that allows a portion of the cross-pin 100 to remain outside of the sleeve 70 while the remainder of the cross-pin 100 extends through the transverse tunnel 66, through the graft 80, and completely across the femoral tunnel 62. Once the ligament graft 80 is temporarily secured within the femoral tunnel 62 using the cross-pin 100, the sleeve 70 can be removed leaving the cross-pin 100 in place, as shown in FIG. 7. The second end of the ligament graft 80 can also be tensioned and secured within the tibial tunnel 52 using the same anchoring technique, or using other anchoring techniques known in the art. When the adhesive 98 is finally cured, the cross-pin 100 can be removed leaving the ligament graft fixed within the femoral tunnel 62, as shown in FIG. 8.

A person skilled in the art will appreciate that the cross-pin 100 can have a variety of configurations, and that various other fixation devices known in the art can be used. For example, while an elongate rod is shown, in other embodiments the fixation device can be in the form of a screw or other anchoring element. The fixation device can also be formed from a variety of materials, but in certain exemplary embodiments it is preferably formed from or coated with a material that prevents adhesion to the adhesive. For example, the fixation device can be formed from or coated with a fluoropolymer plastic resin, such as Teflon®. A person skilled in the art will appreciate that a variety of other materials can be used to prevent adhesive between the cross-pin and the adhesive. The sleeve 70 can also optionally be formed from or coated with a protective material that prevents adhesive to the adhesive.

The materials used to form the adhesive can also vary, and virtually any bone glue or cement known in the art can be used. Since a cross-pin is temporarily used to maintain the ligament graft within the femoral tunnel while the adhesive dries, the drying time for the adhesive can significantly vary and the surgeon has more freedom to select a desired adhesive. The adhesive can also be bioabsorbable or non-absorbable. In certain exemplary embodiments, the adhesive preferably has a viscosity that allows it to be injected into the femoral tunnel without the adhesive dripping, but that allows it to spread around the ligament graft as the graft is pulled fully into the femoral tunnel. By way of non-limiting example, exemplary adhesives include bone glues, such as biocompatible bone glues including 2-octyl cyanoacrylate and the like and equivalent thereof, bone cements, such as conventional biocompatible bone cements including polymethylmethacrylate and the like, as well as dental implant cements such as Premiere Dental Implant Cements.

Figure 12A:
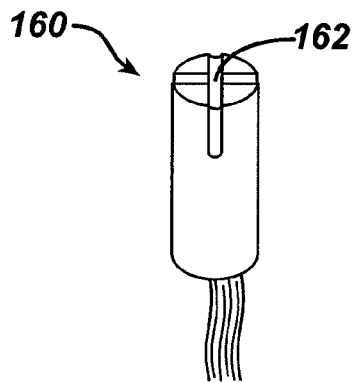
FIG. 12A is a perspective view of one exemplary embodiment of a bone graft modified to have a cross-shaped cut-out for receiving adhesive therein.
Figure 12B:
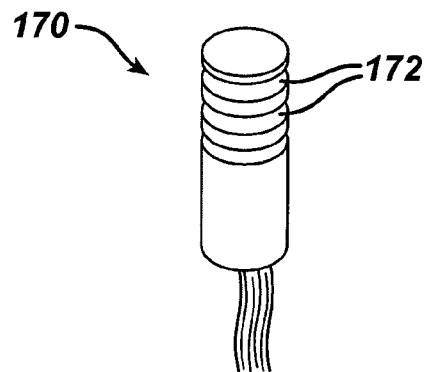
FIG. 12B is a perspective view of another exemplary embodiment of a bone graft modified to have annular grooves for receiving adhesive therein.
Figure 12C:
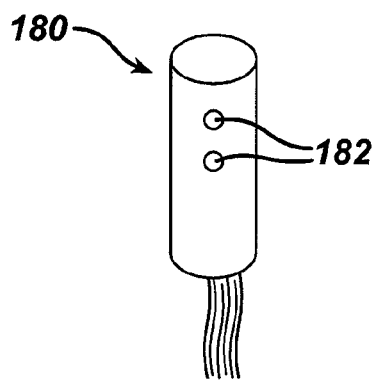
FIG. 12C is a perspective view of yet another exemplary embodiment of a bone graft modified to have thru-bores features for receiving adhesive therethrough.
Figure 12D:
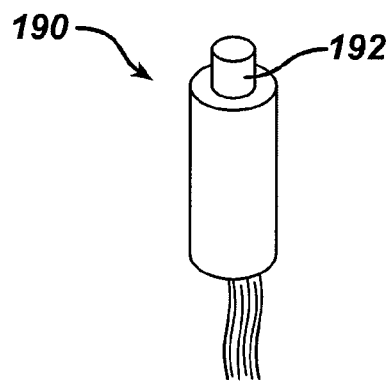
FIG. 12D is a perspective view of another exemplary embodiment of a bone graft modified to have a post formed thereon for receiving adhesive therearound.
Figure 13:
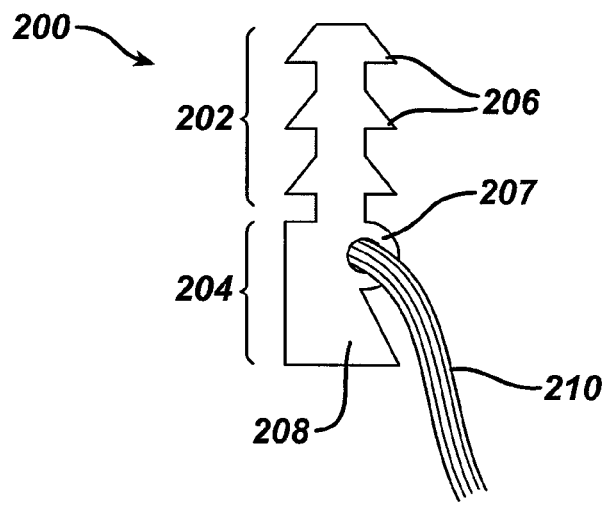
FIG. 13 is a perspective view of yet another embodiment of an anchor having surface features for receiving adhesive therearound, and having a mating element for mating to a ligament graft.

As previously indicated, the ligament graft can also have a variety of configurations, and it can be directly affixed within the bone tunnel, or an anchoring element can be used to affix the ligament graft within the bone tunnel. FIGS. 9A-13 illustrates various exemplary embodiments of ligaments grafts. In the embodiments shown in FIGS. 9A-11C, each ligament graft is in the form of a bone-to-bone graft that is mated to an anchoring element having surface features that facilitate adhesion thereof within a bone tunnel. In the embodiments shown in FIGS. 12A-12D, each ligament graft is also in the form of a bone-to-bone graft, however, rather than using an anchoring element, the bone graft is modified to include surface features to facilitate adhesive thereof within a bone tunnel. FIG. 13 illustrates yet another embodiment of a ligament graft in the form of a soft tissue graft that is attached to an anchoring element having surface features adapted to facilitate adhesive thereof within a bone tunnel. A person skilled in the art will appreciate that the ligament graft can have a variety of other configurations, and that any combination of these features or other features known in the art can be used. Moreover, the various ligament grafts can be implanted using the techniques previously described herein, or they can be implanted using various other techniques known in the art.

Figure 9A:
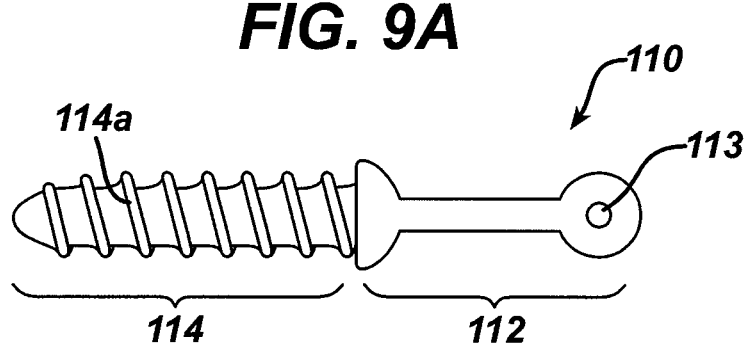
FIG. 9A is a side perspective view of one exemplary embodiment of an anchor configured to mate to a bone graft and to be affixed within a bone tunnel.
Figure 9B:
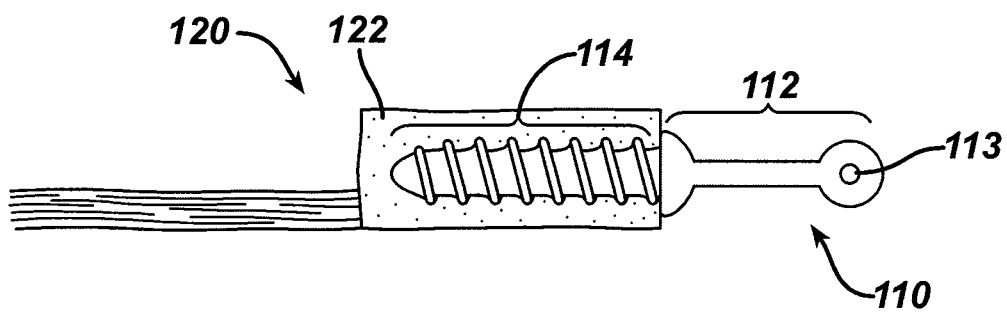
FIG. 9B is a side perspective view of the anchor shown in FIG. 9A mated to a bone graft with a ligament graft extending therefrom.
Figure 9C:
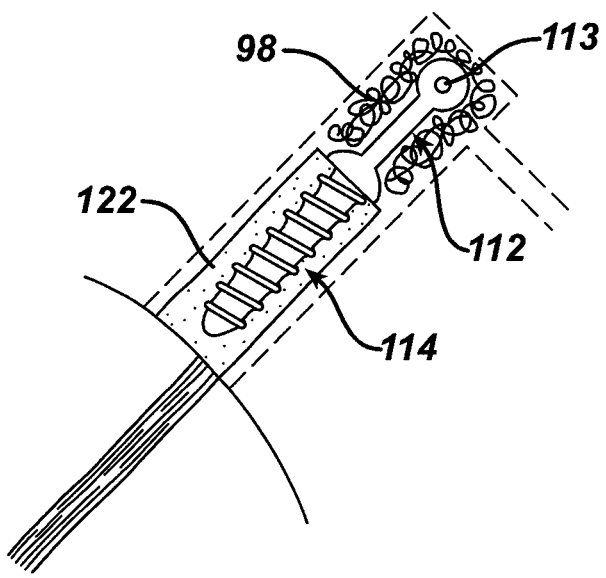
FIG. 9C is an illustration showing the anchor, bone graft, and ligament graft of FIG. 9B implanted within a bone tunnel in bone, showing space in the bone tunnel for receiving an adhesive.

As indicated above, in the embodiment shown in FIGS. 9A-9C, an anchoring element 110 can be used to affix a bone-to-bone graft 120 within a bone tunnel. While the anchoring element 110 can have a variety of configurations, in one exemplary embodiment it preferably includes a first portion 112 that is adapted to be adhesively mated to a bone tunnel, and a second portion 114 that extends from the first portion 112 and that is adapted to mate to a bone graft 122 of a bone-to-bone graft 120.

The first portion 112 can have a variety of configurations, and various techniques can be used to facilitate adhesion between the first portion 112 and a bone tunnel. In the illustrated embodiment, the first portion 112 is in the form of a post having an eyelet formed on a terminal end thereof. The eyelet includes an opening 113 formed therein for receiving a suture which can be used to pull the anchor 110 and ligament graft 120 attached thereto into a bone tunnel. The eyelet, as well as the post, can also facilitate adhesion of the first portion 112 to a bone tunnel, as an adhesive will surround the post and extend into the eyelet, as shown in FIG. 9C. A person skilled in the art will appreciate that the first portion can have a variety of other shapes, and it can include a variety of other features formed thereon, such as grooves, bores, protrusions, etc.

The second portion 114 of the anchor 110 can also have a variety of configurations, and various techniques can be used to mate the second portion 114 to a bone graft 122. As shown in FIGS. 9A-9C, the second portion 114 includes threads 114a formed thereon for allowing the second portion 114 to be threaded into the bone graft 120, as shown in FIG. 9B. Other mating techniques, including adhesives, can be used to mate the second portion 114 to the bone graft 122.

FIG. 10 illustrates another embodiment of an anchor 130 that is adapted to mate to a bone graft, and that is adapted to be affixed within a bone tunnel using an adhesive. The anchor 130 is similar to the anchor 110 shown in FIG. 9A as it includes a first portion 132 having a post and an eyelet, and a second portion 134 adapted to mate to a bone graft. In this embodiment, however, the second portion 134 includes annular cut-out regions 116 formed along a length thereof for receiving an adhesive. The adhesive can be injected into and around the cut-out regions 116 and the second portion 134 can be inserted into a bore drilled in a bone graft to adhere the second portion 134 to the bone graft.

FIGS. 11A-11C illustrate yet another embodiment of an anchor 140 adapted to mate to a bone graft 152 of a bone-to-bone ligament graft 50, and to be adhered within a bone tunnel. Similar to the embodiments shown in FIGS. 9A-10, the anchor 140 includes a first portion 142 having a post and an eyelet formed thereon, and a second portion 144 that is adapted to mate to a bone graft. In this embodiment, the second portion 144 includes opposed arms 145a, 145b that are adapted to receive a bone graft 152 therebetween. While the arms 145a, 145b can optionally be adhesively mated to the bone graft 152, the arms 145a, 145b can also or alternatively be sutured to the bone graft 152. Thus, the opposed arms 145a, 145b can each include one or more thru-bores formed therein. FIGS. 11A-11C illustrate two thru-bores 144a, 144b formed in each arm 145a, 145b. Two corresponding thru-bores 152a, 152b can also be drilled through the bone graft 152 to allow suture 146a, 146b to extend through the bone graft 152 to attach the bone graft 152 to the arms 145a, 145b, as shown in FIG. 11C. A person skilled in the art will appreciate that various other techniques can be used to mate the bone graft 152 to the arms 145a, 145b, and that the arms 145a, 145b can have a variety of other configurations. For example, the arms 145a, 145b can threadably engage the bone graft 152.

In use, the anchoring elements 110, 130, 140 of FIGS. 9A-11C can be implanted within a bone tunnel using various methods known in the art. In an exemplary embodiment, however, the anchors 110, 130, 140 are affixed within a bone tunnel using the exemplary methods previously described herein. In particular, after the anchoring element 110, 130, 140 is attached to a bone graft, the anchoring element 110, 130, 140 can be pulled through the tibial tunnel and at least partially into the femoral tunnel. This can be achieved using various techniques, for example, by tensioning a suture that is attached to the eyelet of the anchor. An adhesive, e.g., adhesive 98 as shown in FIG. 9C, can then be introduced into the femoral tunnel, preferably via the transverse tunnel, to fill a terminal end portion of the femoral tunnel. The anchor 110, 130, 140 can be further pulled into the femoral tunnel, causing the adhesive to spread around the first portion of the anchor 110, 130, 140. Alternatively, the anchor 110, 130, 140 can be fully pulled up into the femoral tunnel prior to introducing the adhesive. While not necessary, a cross-pin can optionally be inserted through the hole in the eyelet to maintain the anchor 110, 130, 140, and thus the ligament graft, within the femoral tunnel until the adhesive cures. Where a cross-pin is not used, a fast drying adhesive is preferably used to allow the other end of the ligament to be anchored in the tibial tunnel without having to wait an extended period of time for the adhesive to cure.

In other embodiments, as previously discussed, the bone graft itself can be modified to be adhesively affixed within a bone tunnel. FIGS. 12A-12D illustrate various exemplary embodiments of such bone grafts. In general, each bone graft, which includes a ligament attached thereto, is modified to include surface features formed thereon for receiving an adhesive therein. Such a configuration allows the adhesive to completely surround and extend into the bone graft, thereby providing a secure connection between the bone graft and the bone tunnel. The shape, quantity, size, and configuration of the surface features can vary. FIG. 12A illustrates one embodiment of a bone graft 160 having a cross-shaped groove 162 formed in a terminal end thereof. The grooves can also extend along at least a portion of the sidewall of the bone graft 160, as shown. In the embodiment shown in FIG. 12B, the bone graft 170 includes annular cut-out portions 172 formed therearound and spaced apart from one another along at least a portion of a length of the bone graft 170. FIG. 12C illustrates yet another embodiment of a bone graft 180 having thru-bores 182 extending therethrough for receiving the adhesive therein. In yet another embodiment, shown in FIG. 12D, the bone graft 190 is modified to include a reduced diameter region 192 such that the bone graft includes a small post formed thereon. In each of the embodiments, the cut-out portions can be formed using instruments and techniques known in the art. In use, the cut-out portions allow the adhesive to extend therein and surround the bone graft, thereby mating the bone graft to the bone tunnel. The bone grafts can be implanted using techniques previously described, or using other techniques known in the art.

FIG. 13 illustrates another embodiment of a ligament graft. In this embodiment, the ligament graft is in the form of a soft tissue graft 210 that does not include a bone graft. The soft tissue graft is mated directly to an anchor 200. The configuration of the anchor 200 can vary, and various techniques can be used to mate the soft tissue graft 210 to the anchor 200. In the illustrated embodiment, the anchor 200 generally includes a first portion 202 that is adapted to adhesively mate to a bone tunnel, and a second portion 204 that is adapted to mate to the soft tissue graft 210. The configuration of the first portion 202 can vary, but it preferably includes features that facilitate mating thereof to a bone tunnel. Any of the features previously described can be used herein, including annular cut-out portions, as shown. In this embodiment, the cut-out portions define flanges 206 which can help maintain the anchor 200 within the bone tunnel, at least temporarily until an adhesive is disposed therearound and cured to lock the anchor 200 in place. The second portion 204 of the anchor can also vary, and it can have virtually any shape and size that facilitates attachment of a soft tissue graft 210 thereto. As shown in FIG. 13, the second portion 204 includes an eyelet 207 formed thereon for receiving the soft tissue graft 210. The second portion 204 also includes a wedge-shaped body 208 extending distally therefrom. The wedge-shaped body 208 can help prevent back-out of the anchor 200 once the anchor is inserted in a bone tunnel. In particular, when tension is applied to the soft tissue graft 210, the soft tissue graft 210 will cause the anchor 200 to pivot. As a result, the wedge-shaped body 208 will extend into and engage the wall of the bone tunnel, thereby preventing movement of the anchor 200 within the bone tunnel. A person skilled in the art will appreciate that the anchor 200 can have a variety of other configurations, and that it does not need to include any features to facilitate back-out or to maintain the anchor 200 in a fixed position, as an adhesive can be used to lock the anchor 200 within the bone tunnel. In use, the anchor 200 can be implanted using techniques previously described, or using other techniques known in the art.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for fixing a ligament graft in a bone tunnel, comprising:
    inserting a ligament graft at least partially into a first bone tunnel formed in a femur or tibia;
    introducing an adhesive into the first bone tunnel;
    inserting a fixation device through a transverse tunnel that intersects the first bone tunnel, the fixation device temporarily maintaining a first end of the ligament graft in the first bone tunnel in contact with the adhesive as the adhesive is curing;

tensioning the ligament graft and fixing a second end of the ligament graft in a second bone tunnel formed in the other one of the femur or tibia; and removing the fixation device once the adhesive is cured.

2. The method of claim 1, wherein the first bone tunnel includes an end wall formed therein.

3. The method of claim 2, wherein the transverse tunnel intersects the first bone tunnel adjacent the end wall.

4. The method of claim 3, wherein the adhesive is introduced through the transverse tunnel such that the adhesive is disposed adjacent to the end wall of the first bone tunnel.

5. The method of claim 4, wherein the ligament graft is positioned a distance apart from the end wall of the first bone tunnel prior to introducing the adhesive, and wherein the ligament graft is pulled toward the end wall and into contact with the adhesive after the adhesive is introduced into the first bone tunnel.

6. The method of claim 1, wherein the ligament graft is pulled through the first bone tunnel using a suture attached thereto.

7. The method of claim 6, wherein, prior to inserting a fixation device, the suture is tensioned to pull the first end of the ligament graft into the adhesive.

8. The method of claim 1, wherein the fixation device is inserted through a loop formed on the ligament graft.

9. The method of claim 1, wherein the ligament graft includes an anchor coupled to at least one of the first and second ends thereof.

10. The method of claim 1, wherein an anchor is coupled to the first end of the ligament graft, and wherein the fixation device is inserted into the anchor to maintain the first end of the ligament graft in the femoral tunnel.

11. The method of claim 1, wherein the fixation device includes a protective coating disposed thereon and adapted to prevent adhesion between the adhesive and the cross-pin.

12. The method of claim 11, wherein the protective coating is formed from a fluoropolymer plastic resin.

13. The method of claim 1, wherein the adhesive is introduced through a sleeve disposed at least partially through the first bone tunnel.

14. The method of claim 1, wherein the adhesive is selected from the group consisting of a bioabsorbable adhesive and a non-absorbable adhesive.

15. The method of claim 1, wherein the fixation device comprises a cross-pin.

16. The method of claim 1, wherein the ligament graft includes a bone graft coupled thereto and an anchor mated to the bone graft.

17. A method for fixing a ligament graft in a bone tunnel, comprising:

inserting a ligament graft at least partially into a first tunnel formed in bone;

introducing an adhesive into the first tunnel;

inserting a fixation device through a second tunnel that intersects the first tunnel to temporarily maintain the ligament graft in contact with the adhesive as the adhesive is curing; and removing the fixation device once the adhesive is cured such that the ligament graft is fixed in the tunnel.

18. The method of claim 17, further comprising, prior to removing the fixation device, applying tension to a free end of the ligament graft and securing the free end of the ligament graft in a second tunnel formed in bone.

19. The method of claim 17, wherein the first tunnel includes an end wall formed therein, the ligament graft being fixedly attached to the end wall.

20. The method of claim 19, wherein the adhesive is introduced through a separate tunnel and is disposed adjacent to the end wall.

21. The method of claim 20, wherein the ligament graft is pulled into contact with the adhesive after the adhesive is disposed adjacent to the end wall of the first tunnel.

22. The method of claim 17, wherein the fixation device comprises a cross-pin that is inserted through a loop formed on the ligament graft.

23. The method of claim 17, wherein the adhesive is selected from the group consisting of a bioabsorbable adhesive and a non-absorbable adhesive.

24. The method of claim 17, wherein the fixation device includes a protective coating disposed thereon and adapted to prevent adhesion between the adhesive and the fixation device.

25. The method of claim 17, wherein the ligament graft includes a bone graft coupled thereto and an anchor mated to the bone graft.

26. The method of claim 25, wherein the adhesive surrounds the anchor.

27. The method of claim 25, wherein the fixation device is inserted through the anchor.

* * * * *